(12) United States Patent
Kim et al.

(10) Patent No.: US 8,889,386 B2
(45) Date of Patent: Nov. 18, 2014

(54) METHOD FOR PRODUCING BIO-ALCOHOL USING NANOPARTICLES

(71) Applicant: Hankyong Industry Academic Cooperation Center, Gyeonggi-do (KR)

(72) Inventors: Young-Kee Kim, Gyeonggi-do (KR); Soeun Park, Gyeonggi-do (KR); Jinwon Lee, Seoul (KR)

(73) Assignee: Hankyong Industry Academic Cooperation Center, Gyeonggi-Do (KR)

( * ) Notice: Subject to any disclaimer, the term of this patent is extended or adjusted under 35 U.S.C. 154(b) by 0 days.

(21) Appl. No.: 13/869,677

(22) Filed: Apr. 24, 2013

(65) Prior Publication Data

US 2014/0308722 A1 Oct. 16, 2014

(30) Foreign Application Priority Data

Apr. 11, 2013 (KR) .......................... 10-2013-0039591

(51) Int. Cl.
*C12P 7/06* (2006.01)

(52) U.S. Cl.
USPC .............................................. 435/161; 977/773

(58) Field of Classification Search
USPC .............................................. 435/161; 977/773
See application file for complete search history.

(56) References Cited

U.S. PATENT DOCUMENTS

2009/0035848 A1\* 2/2009 Hickey ........................ 435/296.1

FOREIGN PATENT DOCUMENTS

KR 10-2006-0110868 10/2006

\* cited by examiner

*Primary Examiner* — Rosanne Kosson
(74) *Attorney, Agent, or Firm* — Alston & Bird LLP

(57) ABSTRACT

Disclosed is a method for producing a bioalcohol based on the fermentation of syngas. The method includes adding hydrophilic nanoparticles surface modified with hydrophobic groups to a culture medium for fermentation. Also disclosed are hydrophilic nanoparticles surface modified with hydrophobic groups for enhancing bioalcohol yield. The hydrophilic nanoparticles may be, for example, silica nanoparticles.

12 Claims, 7 Drawing Sheets

METHOD FOR PRODUCING BIO-ALCOHOL USING NANOPARTICLES

BACKGROUND OF THE INVENTION

1. Field of the Invention

The present invention relates to a method for producing a bioalcohol. More specifically, the present invention relates to a method for increasing the productivity of a bioalcohol in which hydrophobically modified hydrophilic nanoparticles, such as silica nanoparticles, are used to enhance the solubility of syngas in a fermentation process.

2. Description of the Related Art

Bioenergy has been most widely developed and utilized in recent years due to its potential to replace fossil fuels. Particularly, lignocellulosic biomass-based ethanol production technology has an advantage in that raw materials therefor are abundant anddiverse.

Major methods for producing bioethanol from lignocellulosic biomass include a saccharification-fermentation processand a gasification-fermentation process. According to the saccharification-fermentation process, pretreated lignocellulosic biomass is saccharified by hydrolysis and fermented to produce ethanol. According to the gasification-fermentation process, lignocellulosic biomass is gasified to produce syngas composed of carbon monoxide, carbon dioxide, and hydrogen, followed by fermentation of the syngas to produce ethanol. The saccharification-fermentation process involves complex pretreatment and hydrolysis steps to produce monosaccharides, which are used in subsequent fermentation. Accordingly, the saccharification-fermentation process is disadvantageous in terms of time and cost. In contrast, the gasification-fermentation process does not require saccharification and is thus advantageous in that ethanol can be obtained in a relatively simple manner. Another advantage of the gasification-fermentation process is that the gasification is independently used for heat/power production because syngas can be used as an electricity or heat energy source through combustion. Raw materials for syngas production can be extended to organic waste, such as agricultural waste, as well as lignocellulosic biomass.

Particularly, research on the production of valuable substances from syngas is extremely limited. A catalytic reaction may be used as achemical method for the production of a valuable substance from syngas. In this case, since the reaction is highly sensitive to the presence of small amounts of impurities, syngas containing large amounts of impurities should undergo purification to produce a valuable substance, such as a synthetic oil. Alternatively, a biological method may be applied to the production of a valuable substance from syngas. The biological method does not require highly pure reactants, unlike catalytic reaction. Therefore, the syngas can be directly used without further purification. The reaction is carried out under ambient temperature and pressure conditions, which is advantageous in terms of initial investment and operating costs.

Carbon monoxide, carbon dioxide, and hydrogen are converted into various substances by aerobic or anaerobic microorganisms. Some anaerobic microorganisms were reported to have the ability to produce ethanol from carbon monoxide, carbon dioxide and hydrogen substrates. Particularly representative examples of such microorganisms include *Clostridium ljungdahlii, Eubacterium limosum*, and *Peptostreptococcus productus*.

However, it is very difficultfor microorganisms to utilize carbon monoxide, carbon dioxide, and hydrogen as main substrates for biological conversion due to extremely low solubilities thereof. For this reason, the conversion of the gases into organic acids or bioalcohols such as ethanol remains at a negligible level, which limits its application to mass production.

PRIOR ART DOCUMENT(S)

Patent Document(s)

Korean Patent Publication No. 10-2006-0110868

SUMMARY OF THE INVENTION

It is an object of the present invention to provide a method for producing a bioalcohol that uses hydrophobically surface-modified silica nanoparticles to achieve enhanced production yield.

According to one aspect of the present invention, there is provided a method for producing a bioalcohol from syngas by fermentation, the method including adding silica nanoparticles having surface modified with hydrophobic groups to a culture medium for the fermentation.

According to another aspect of the present invention, there is provided a bioalcohol produced by the method.

According to the method of the present invention, the hydrophilicity of hydrophilic nanoparticles, such as silica nanoparticles, is controlled by surface modification to improve the mass transfer of individual gas substrates. Therefore, the method of the present invention can be applied to the production of a bioalcohol based on the fermentation of syngas, achieving enhanced yield of the bioalcohol.

BRIEF DESCRIPTION OF THE DRAWINGS

These and/or other aspects and advantages of the invention will become apparent and more readily appreciated from the following description of the embodiments, taken in conjunction with the accompanying drawings of which.

DETAILED DESCRIPTION OF THE INVENTION

The present invention will now be described in detail.

The present invention provides a method for producing a bioalcohol from syngas by fermentation, the method including adding silica nanoparticles having surface modified with hydrophobic groups to a culture medium for fermentation.

The hydroxyl groups of the silica nanoparticles are substituted with $C_1$-$C_4$ alkyl groups as the hydrophobic groups. The $C_1$-$C_4$ alkyl groups are preferably methyl groups, which have less steric hindrance in the reaction.

A weight ratio of carbon atoms in the silica nanoparticles having surface modified with methyl groups is preferably in the range of 4-5 wt %. Within this range, enhanced solubility of gases can be obtained.

The silica nanoparticles may be prepared by stirring a mixture of an aqueous ethanol solution, tetraethyl orthosilicate, and ammonium hydroxide.

The surface modification of silica nanoparticles having surface modified with methyl groups are prepared by adding 30 to 150 parts by weight, preferably 40 to 100 parts by weight of triethoxymethylsilane to 1 part by weight of the silica nanoparticles.

Figure 1:
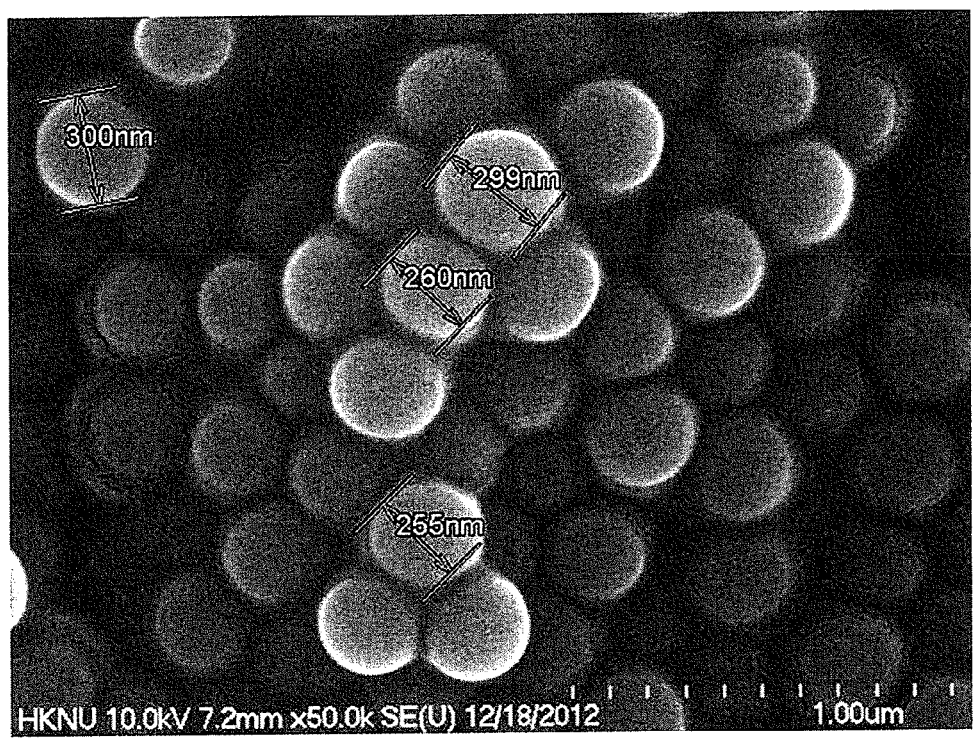
FIG. 1 is a scanning electron microscopy (SEM) image of silica nanoparticles prepared in Preparative Example 1.
Figure 2:
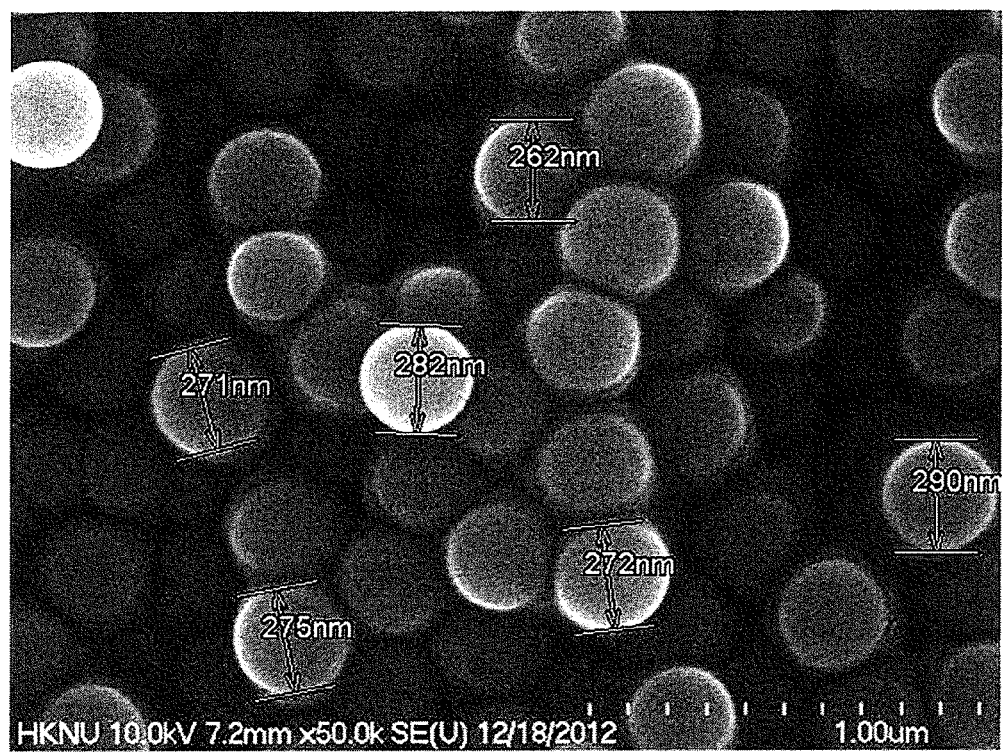
FIG. 2 is a SEM image of silica nanoparticles surface modified with methyl groups prepared in Example 1.

The silica nanoparticles having surface modified with hydrophobic groups have an average particle size of 100 to 500 nm, preferably 200 to 400 nm, more preferably 250 to 300 nm. The particles should be present at gas-liquid interfaces where catalytic reaction takes place. The gas-liquid interface layers are usually 5 to 25 μm thick. When the particle size is less than or equal to the thickness of the gas-liquid interface layers, a catalytic reaction predominantly occurs. FIGS. 1 and 2 show the shapes and sizes of the nanoparticles before and after surface modification with methyl groups.

The silica nanoparticles having surface modified with hydrophobic groups may be added in an amount of 0.1 to 1 part by weight, preferably 0.1 to 0.5 parts by weight, more preferably 0.2 to 0.4 parts by weight, based on 100 parts by weight of the culture medium. If the amount of the surface-modified silica nanoparticles is smaller than the lower limit, substantial catalytic activity of the surface-modified silica nanoparticles cannot be expected. Meanwhile, the addition of the surface-modified silica nanoparticles in an amount exceeding the upper limit does not contribute to further increase of solubility.

The syngas is composed of hydrogen, carbon monoxide, and carbon dioxide. The syngas may be prepared by gasification of coal or biomass, or by subjecting waste gas or flue gas to at least one treatment method selected from radiation, sonication, and pyrolysis.

Anaerobic bacteria may be used as microorganisms for the production of a bioalcohol. *Clostridium ljungdahlii, Clostridium thermoaceticum, Clostridium aceticum, Acetobacterium woodii, Thermoanaerobacterium kivui, Butyribacterium methylotrophicum, Clostridium acetobutylicum, Clostridium formicaceticum, Clostridium kluyveri, Clostridium thermocellum, Clostridium thermosaccharolyticum, Eubacterium limosum*, and *Peptostreptococcus productus* are representative biocatalysts that use carbon monoxide and carbon dioxide as carbon sources and hydrogen as an electron donor to produce ethanol and acetic acid.

Figure 3:
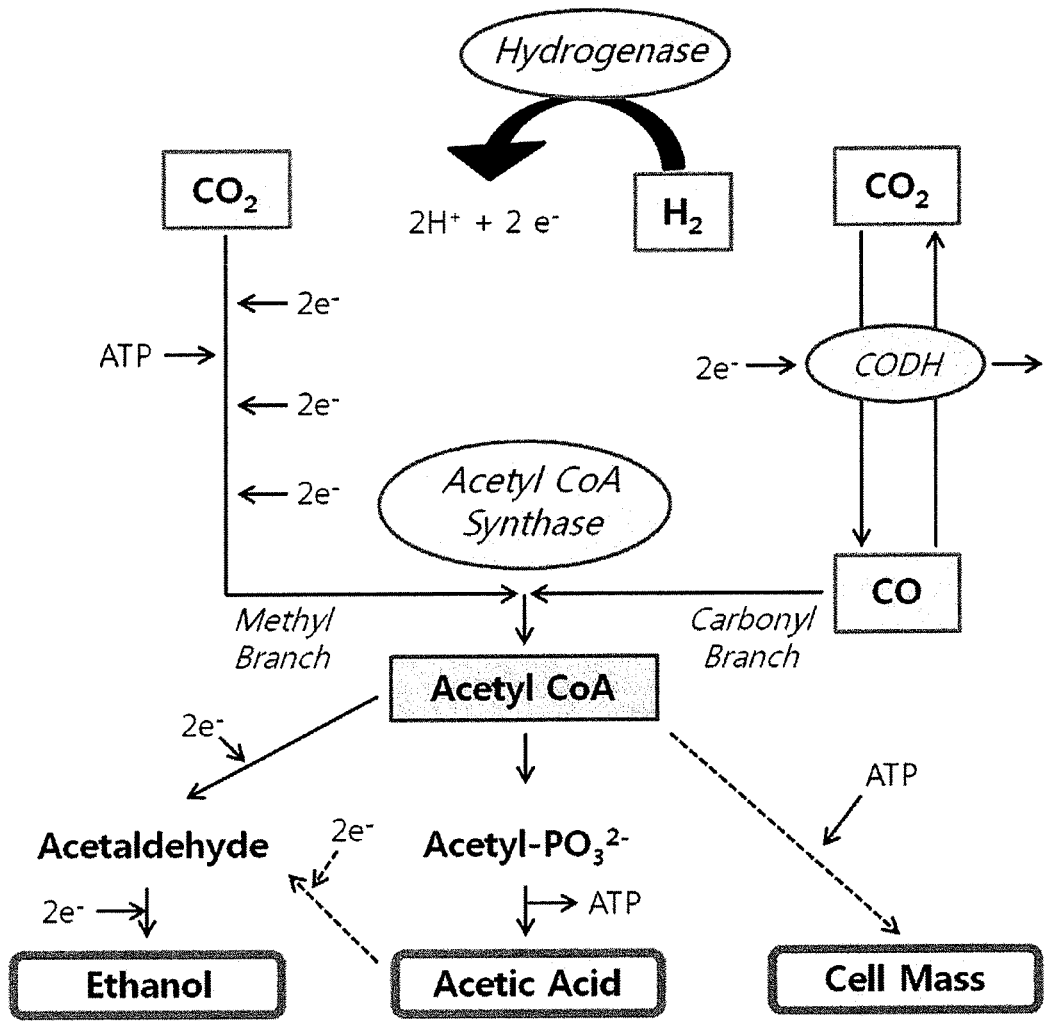
FIG. 3 shows the acetyl-coenzyme A pathway.

These microorganisms can produce ethanol and acetic acid through the acetyl-coenzyme A pathway shown in FIG. 3.

The present invention will be explained in more detail with reference to the following examples. However, it will be appreciated by those skilled in the art that these examples are provided for illustrative purposes and are not intended to limit the scope of the invention.

EXAMPLES

Preparative Example 1

Preparation of Silica Nanoparticles 400 ml of ethanol and 3 ml of tetraethyl orthosilicate were stirred with a magnetic bar for 1 hr. To the mixture was added 30 ml of an aqueous ammonium hydroxide solution. After stirring for 2 hr, the reaction mixture was transferred portionwise (10 ml aliquots) to 15 ml conical tubes and centrifuged at 3000 rpm for 15 min. The supernatant was discarded and the sediment was washed with ethanol to remove impurities. Thereafter, 2 ml of ethanol was added, followed by centrifugation at 3000 rpm for 5 min. After removal of the supernatant, the sediment was washed again and dried at 80° C. for 1.5 hr, affording silica nanoparticles.

A scanning electron microscopy (SEM) image of the silica nanoparticles is shown in FIG. 1. The silica nanoparticles had a particle size of 255-300 nm with an average particle size of 278 nm.

Experimental Example 1

Measurement of Carbon Dioxide Solubilities According to Kind of Nanoparticles

1) Experimental Method

An experimental apparatus for testing the mass transfer of syngas was prepared as follows. First, a 250 ml bottle was filled with 200 ml of distilled water, and then nitrogen gas was injected thereinto to create an oxygen-free environment. Syngas was injected into the bottle until the internal pressure reached 1.2 atm, and the inlet was closed to prevent gas leakage. After stirring with a magnetic bar at a rate of 200 rpm for 5, 10, 15, 20, 25, and 30 min, the concentrations of the syngas in the distilled water at the different times were analyzed to observe dissolution rates. Despite attempts to analyze the concentrations of the gas dissolved in the water according to stirring times, it was difficult to directly measure the gas concentrations because the gas was dissolved at very low concentrations in the water. The vapor-phase gas in the experimental apparatus was collected in a Tedlar bag and analyzed by gas chromatography. The amount of the vapor-phase gas was determined using the gas pressure. The amount of the gas dissolved in the water was indirectly measured by subtracting the vapor-phase gas concentration measured in the course of the experiment from the initial concentration of the gas present in the experimental apparatus.

2) Experimental Results

Figure 4:
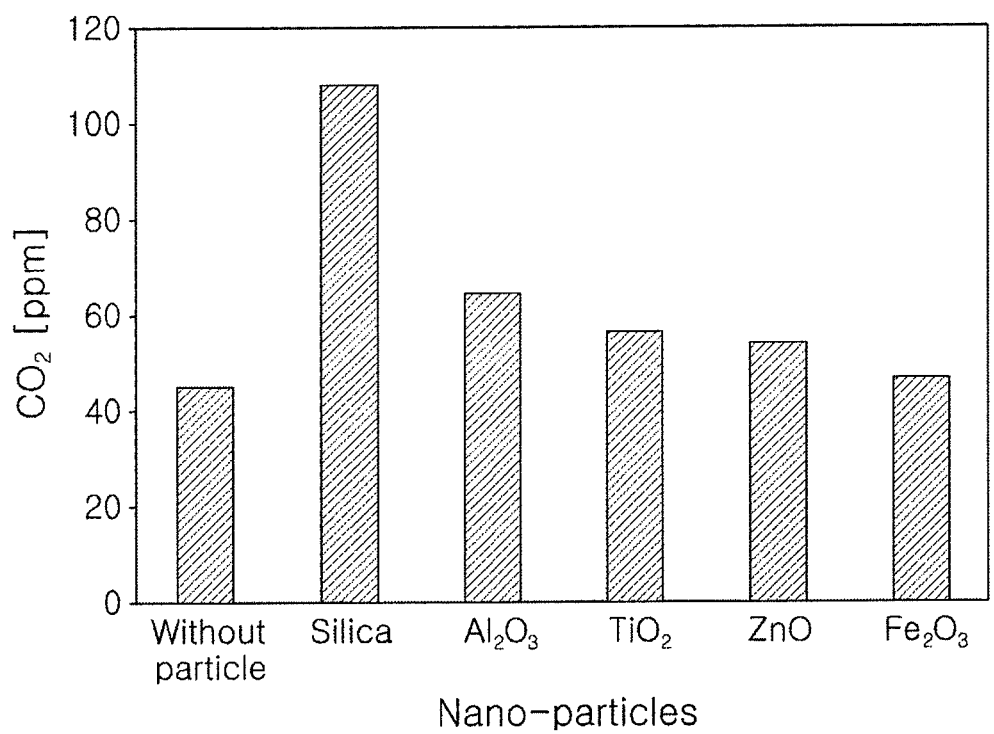
FIG. 4 is a graph showing the concentrations of dissolved carbon dioxide when different kinds of nanoparticles were added in Experimental Example 1.

The silica nanoparticles of Preparative Example 1, aluminum oxide ($Al_2O_3$) nanoparticles (average particle size=280 nm), titanium dioxide ($TiO_2$) nanoparticles (average particle size=280 nm), zinc oxide (ZnO) nanoparticles (average particle size=280 nm), and iron oxide ($Fe_2O_3$) nanoparticles (average particle size=280 nm) were prepared. 0.3 parts by weight of each of the different kinds of nanoparticles were added to 100 parts by weight of distilled water. After injection of carbon dioxide as syngas, the mixture was allowed to react for 20 min. Thereafter, the concentration of dissolved carbon dioxide was measured. The results are shown in FIG. 4. The above procedure was repeated without the addition of nanoparticles ("negative control").

The concentration of dissolved carbon dioxide was 45.04 ppm when nanoparticles were not added, and the concentrations of dissolved carbon dioxide were between 46 and 64 ppm when the aluminum oxide ($Al_2O_3$) nanoparticles, titanium dioxide ($TiO_2$) nanoparticles, zinc oxide (ZnO) nanoparticles, and iron oxide ($Fe_2O_3$) nanoparticles were added. That is, there were no substantial differences in concentration of dissolved carbon dioxide despite the addition of the nanoparticles. In contrast, when the silica nanoparticles of Preparative Example 1 were added, the concentration of dissolved carbon dioxide was 108 ppm, which was approximately two times higher than in the negative control and when the other kinds of nanoparticles were added.

Example 1

Preparation of Silica Nanoparticles Having Surface Modified with Methyl Groups 1

To 1 g of the silica nanoparticles of Preparative Example 1 were added 405 ml of a 95% (v/v) ethanol aqueous solution (ethanol:water=95:5, density 0.8 g/ml) and 45 ml of triethoxymethylsilane (density 0.9 g/ml). The mixture was stirred with a magnetic bar for 12 hr. Thereafter, the reaction mixture was washed with ethanol and dried at 80° C. for 1.5 hr, affording silica nanoparticles having surface modified with methyl groups.

A scanning electron microscopy (SEM) image of the silica nanoparticles having surface modified with methyl groups is shown in FIG. 2. The silica nanoparticles had a particle size of 262-290 nm with an average particle size of 276 nm.

Example 2

Preparation of Silica Nanoparticles Having Surface Modified with Methyl Groups 2

Silica nanoparticles having surface modified with methyl groups were prepared in the same manner as in Example 1, except that 360 ml of a 95% (v/v) ethanol aqueous solution and 90 ml of triethoxymethylsilane were added.

Example 3

Preparation of Silica Nanoparticles Having Surface Modified with Methyl Groups 3

Silica nanoparticles having surface modified with methyl groups were prepared in the same manner as in Example 1, except that 427.5 ml of a 95% (v/v) ethanol aqueous solution and 22.5 ml of triethoxymethylsilane were added.

Experimental Example 2

IR Spectral Analysis

Figure 5:
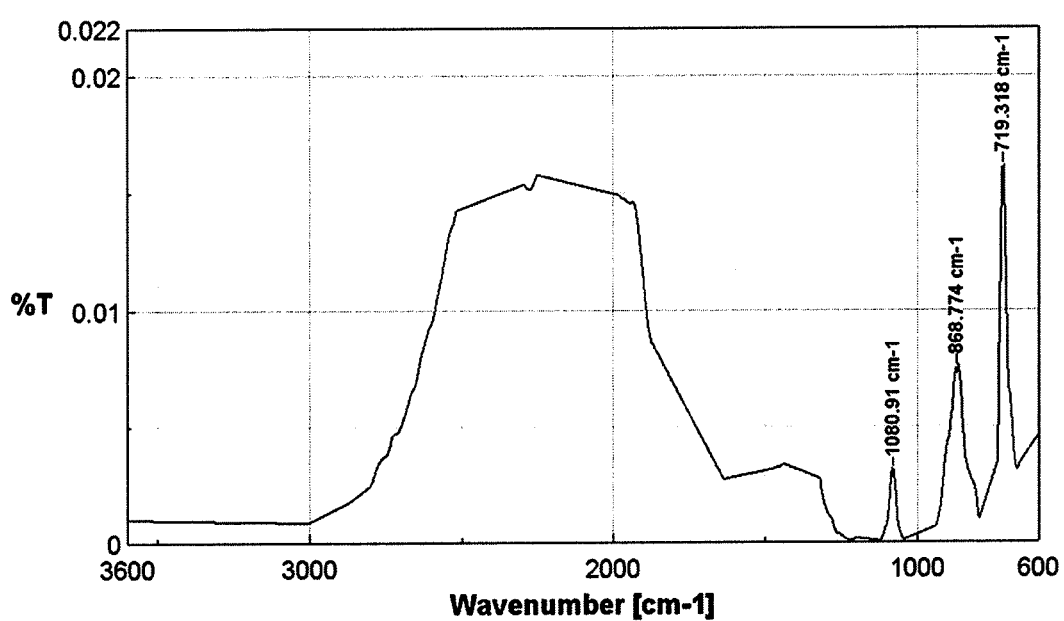
FIG. 5 is an IR spectrum of silica nanoparticles surface modified with methyl groups prepared in Example 1.

An IR spectrum of the silica nanoparticles having surface modified with methyl groups was recorded to confirm whether the silica nanoparticles were substituted with the methyl groups on the surfaces thereof. The spectrum is shown in FIG. 5. Peaks appeared at 1080.91 $cm^{-1}$, 868.774 $cm^{-1}$, and 719.318 $cm^{-1}$, which correspond to Si—O—Si, Si—OH, and Si—$CH_3$, respectively. These spectral data reveal successful synthesis of the silica nanoparticles having surface modified with methyl groups.

Experimental Example 3

Elemental Analysis

An elemental analyzer (Elementar Vario EL cube, Elementar Analysensysteme GmbH) was used to analyze the carbon, hydrogen, nitrogen, and sulfur contents of the silica nanoparticles prepared in Preparative Example 1 and the surface-modified silica nanoparticles of Examples 1-3. The results are shown in Table 1.

The carbon (C)/hydrogen (H) ratios in the surface-modified silica nanoparticles of Examples 1 and 2 were greater than the C/H ratio in the silica nanoparticles of Preparative Example 1. Although two times more triethoxymethylsilane was used in Example 2 than in Example 1, there was no significant difference in the C/H ratio between Examples 1 and 2. The C/H ratio in the silica nanoparticles of Example 3 was relatively low compared to the C/H ratios in the silica nanoparticles of Examples 1-2, demonstrating that the silica nanoparticles of Example 3 had a lower degree of substitution with methyl groups.

TABLE 1

|  | C (wt. %) | H (wt. %) |
| --- | --- | --- |
| Preparative Example 1 | 12.33 | 1.501 |
| Example 1 | 4.33 | 1.985 |
| Example 2 | 4.82 | 2.142 |
| Example 3 | 3.45 | 1.892 |

Example 4

Preparation of Silica Nanoparticles Having Surface Modified with Isopropyl Groups Silica nanoparticles having surface modified with isopropyl groups were prepared in the same manner as in Example 1, except that hexamethyldisilazane was added instead of triethoxymethylsilane.

Experimental Example 4

Measurement of Hydrogen, Carbon Monoxide and Syngas Solubilities Depending on Surface Modification of the Nanoparticles In the same manner as in Experimental Example 1, 0.3 parts by weight of each of the silica nanoparticles of Preparative Example 1, and the surface-modified silica nanoparticles of Examples 1-4 were added to 100 parts by weight of distilled water, and the solubilities of injected gases were measured. The results are shown in Table 2. Hydrogen, carbon monoxide, and syngas were used as the gases. The syngas was a mixture of hydrogen, carbon monoxide, and carbon dioxide in a volume ratio of 20:40:40.

TABLE 2

|  | Hydrogen | Carbon monoxide | Syngas |
| --- | --- | --- | --- |
| Negative control | 0.69 | 45.04 | 103.66 |
| Preparative | 1.4 | 108 | 236 |

TABLE 2-continued

|  | Hydrogen | Carbon monoxide | Syngas |
|---|---|---|---|
| Example 1 |  |  |  |
| Example 1 | 11.8 | 168 | 311 |
| Example 2 | 11.0 | 184 | 332 |
| Example 3 | 4.2 | 125 | 269 |
| Example 4 | 10.6 | 133 | 260 |

The concentration of dissolved hydrogen when the silica nanoparticles of Example 1 were added was 17.1 times higher than in the negative control and 8.4 times higher than when the silica nanoparticles of Preparative Example 1 were added. The concentration of dissolved carbon monoxide when the silica nanoparticles of Example 1 were added was 3.7 times higher than in the negative control and 1.6 times higher than when the silica nanoparticles of Preparative Example 1 were added. The concentration of dissolved syngas when the silica nanoparticles of Example 1 were used was 3 times higher than in the negative control and 1.2 times higher than when the silica nanoparticles of Preparative Example 1 were added.

The addition of the silica nanoparticles of Example 2 led to higher dissolved hydrogen, carbon monoxide and syngas concentrations. In contrast, all of the gases were dissolved at lower concentrations when the silica nanoparticles of Example 3 were added than when the silica nanoparticles of Examples 1 and 2 were added. These results are assumed to be due to the lower degree of substitution with methyl groups in the silica nanoparticles of Example 3, which was confirmed through the elemental analysis results in Table 1.

The concentrations of the dissolved gases in Example 4 were slightly lower than those in Example 1, but were considerably enhanced compared to those in the negative control and Preparative Example 1.

Experimental Example 5

Figure 6:
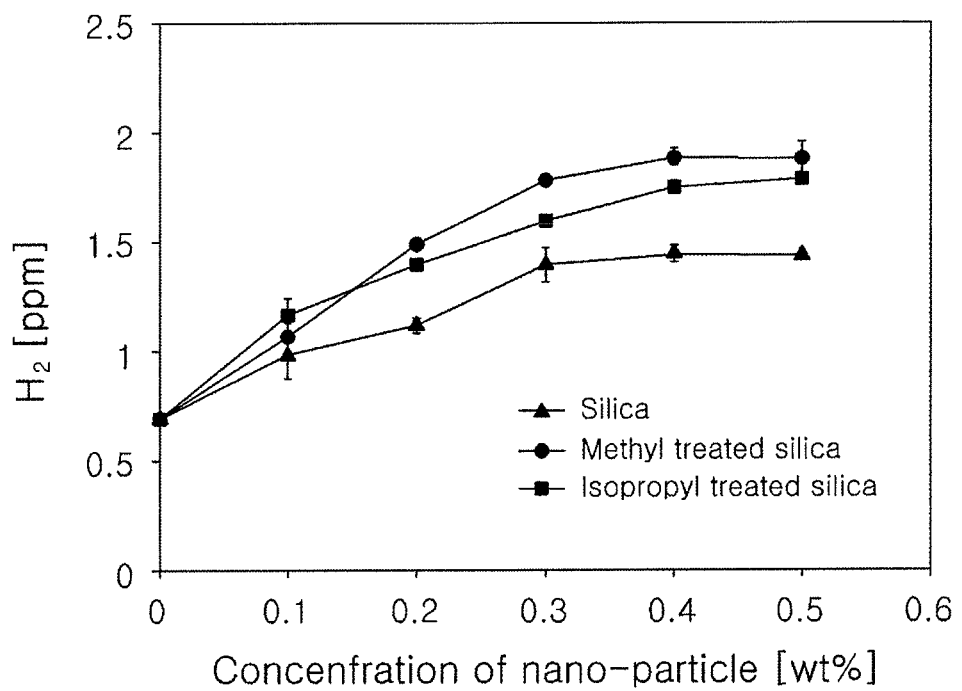
FIG. 6 is a graph showing changes in the concentration of dissolved hydrogendepending on the concentrations of silica nanoparticles prepared in Preparative Example 1, silica nanoparticles surface modified with methyl groups prepared in Example 1, and silica nanoparticles surface modified with isopropyl groups prepared in Example 4.
Figure 7:
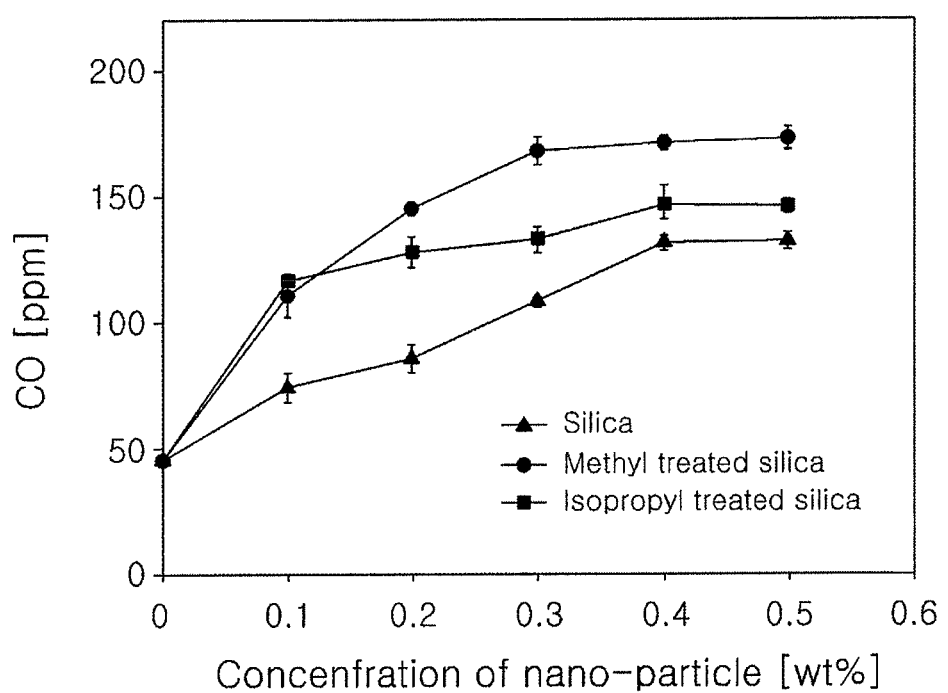
FIG. 7 is a graph showing changes in the concentration of dissolved carbon monoxide depending on the concentrations of silica nanoparticles prepared in Preparative Example 1, silica nanoparticles surface modified with methyl groups prepared in Example 1, and silica nanoparticles surface modified with isopropyl groups prepared in Example 4.
Figure 8:
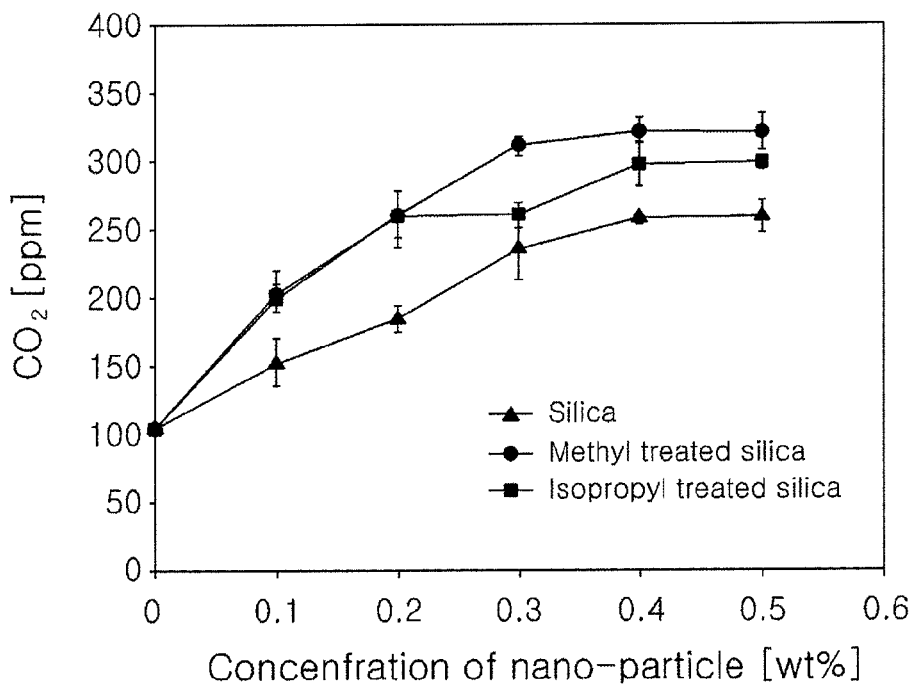
FIG. 8 is a graph showing changes in the concentration of dissolved carbon dioxide depending on the concentrations of silica nanoparticles prepared in Preparative Example 1, silica nanoparticles surface modified with methyl groups prepared in Example 1, and silica nanoparticles surface modified with isopropyl groups prepared in Example 4.

Solubilities of Gases Depending on the Concentrations of the Surface-Modified Silica Nanoparticles Different amounts (0.1, 0.2, 0.3, 0.4, and 0.5 parts by weight) of each of the silica nanoparticles of Preparative Example 1, the surface-modified silica nanoparticles of Example 1, and the surface-modified silica nanoparticles of Example 4 were dispersed in 100 parts by weight of distilled water. The solubilities of hydrogen, carbon monoxide, and carbon dioxide in the dispersions were measured. FIGS. 6 to 8 are graphs showing the solubilities of hydrogen, carbon monoxide, and carbon dioxide depending on the concentrations of the silica nanoparticles of Preparative Example 1 (▲), the surface-modified silica nanoparticles of Example 1 (●), and the surface-modified silica nanoparticles of Example 4 (■).

No significant differences were observed in the concentration of dissolved hydrogen gas when the nanoparticles of Preparative Example 1 and Examples 1 and 4 were added in amounts of 0.1 parts by weight, but significant differences were observed when the nanoparticles of Preparative Example 1 and Examples 1 and 4 were added in amounts of 0.2 parts by weight or more. The addition of the nanoparticles of Examples 1 and 4 in amounts of 0.4 parts by weight or more did not cause significant increases in the concentration of dissolved hydrogen gas.

The concentrations of dissolved carbon monoxide gas increased two times or more after the silica nanoparticles of Examples 1 and 4 were added in amounts of 0.1 parts by weight. Unlike the case of hydrogen gas, the concentration of dissolved carbon monoxide increased steadily up to the addition of 0.3 parts by weight of the nanoparticles of Example 1, but increased sharply when the nanoparticles of Example 4 were added in an amount of 0.1 parts by weight, and thereafter increased moderately.

The concentration of dissolved carbon dioxide gas increased sharply until the addition of 0.3 parts by weight of the nanoparticles of Example 1, and thereafter increased moderately. The concentration of dissolved carbon monoxide increased sharply until the addition of 0.2 parts by weight of the nanoparticles of Example 4, and thereafter increased moderately.

Experimental Example 6

Measurement of Production Yields of Bioethanol

1) Experimental Method

Syngas composed of 20% hydrogen, 40% carbon monoxide, and 40% carbon dioxide was filled in a glass reaction vessel whose total volume was one liter. *Clostridium ljungdahlii* was inoculated into a culture medium to ferment the syngas. The internal pH of the reactor was maintained at pH 7 using sodium hydroxide and hydrochloric acid. A 2 M aqueous hydrochloric acid solution was added when the pH increased above 7.1, and a 2 M aqueous sodium hydroxide solution was added when the pH decreased below 6.95. For homogenization, stirring was performed with a magnetic bar. At this time, the stirring rate was 180 rpm. Warm water was circulated through a water jacket of the reactor to maintain the internal temperature of the reactor constant at 37° C. The vapor-phase gas in the reactor was collected in a Tedlar bag and analyzed by gas chromatography to measure the concentration of the gas used in the reaction. The amount of the vapor-phase gas was determined using the gas pressure. The produced alcohol was analyzed by GC.

2) Experimental Results

Figure 9:
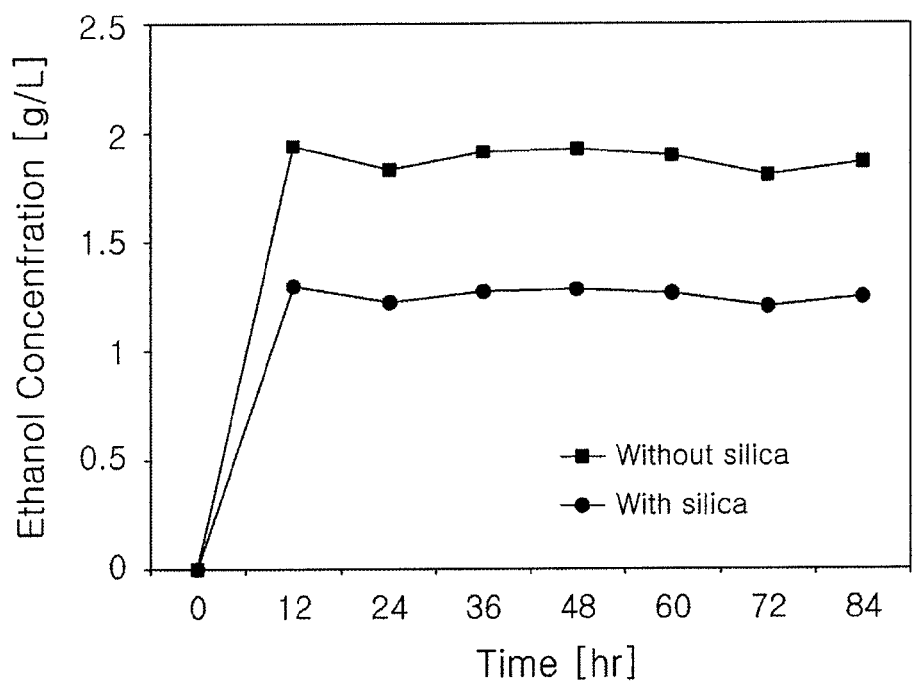
FIG. 9 is a graph showing changes in the concentration of bioethanol produced with and without the addition of 0.3 parts by weight of silica nanoparticles having surface modified with methyl group prepared in Example 1 to 100 parts by weight of the culture medium in a reaction vessel.

When 0.3 parts by weight of the surface-modified silica nanoparticles of Example 1 were added to 100 parts by weight of culture medium in the reaction vessel (■), ethanol began to produce from 12 hr after inoculation, as shown in FIG. 9. The ethanol concentration was 1.93 g/L. There was no substantial change in the ethanol concentration during the reaction for 84 hr.

In contrast, when no nanoparticles were added (●), ethanol began to produce from 12 hr after inoculation. The ethanol concentration was 1.29 g/L.

From these results, it can be confirmed that the addition of the nanoparticles of Example 1 resulted in a 1.5-fold increase in the production yield of bioethanol.

What is claimed is:

1. A method for producing a bioalcohol from syngas by fermentation, the method comprising:
   a) adding silica nanoparticles having a surface modified with hydrophobic groups to a culture medium for the fermentation;
   b) inoculating the culture medium with one or more bacteria that make the bioalcohol from the syngas;
   c) culturing the bacteria of step (b); and
   d) isolating the bioalcohol made in step (c).

2. The method according to claim 1, wherein the hydrophobic groups are bound to the hydroxyl groups of the silica nanoparticles, and wherein the hydrophobic groups are $C_1$-$C_4$ alkyl groups.

3. The method according to claim 2, wherein the hydrophobic groups are methyl groups.

4. The method according to claim 3, wherein the silica nanoparticles are prepared by stirring a mixture of an ethanol aqueous solution, tetramethylorthosilicate, and ammonium hydroxide.

5. The method according to claim 4, wherein the silica nanoparticles having the surface modified with methyl groups are prepared by mixing 30 to 150 parts by weight of triethoxymethylsilane with 1 part by weight of the silica nanoparticles.

6. The method according to claim 1, wherein the silica nanoparticles having the surface modified with hydrophobic groups have an average particle size of 100 to 500 nm.

7. The method according to claim 1, wherein the silica nanoparticles having the surface modified with hydrophobic groups are added in an amount of 0.1 to 1 part by weight, based on 100 parts by weight of the culture medium.

8. The method according to claim 1, wherein the syngas comprises hydrogen, carbon monoxide, and carbon dioxide.

9. The method according to claim 1, wherein the syngas is prepared by gasification of coal or biomass.

10. The method according to claim 1, wherein the syngas is prepared by subjecting waste gas or flue gas to at least one treatment method selected from the group consisting of radiation, sonication, and pyrolysis.

11. The method according to claim 1, wherein the culture medium of step (b) comprises at least one bacterium selected from the group consisting of *Clostridium ljungdahlii, Clostridium thermoaceticum, Clostridium aceticum, Acetobacterium woodii, Thermoanaerobacterium kivui, Butyribacterium methylotrophicum, Clostridium acetobutylicum, Clostridium formicaeetricum, Clostridium kluyveri, Clostridium thermocellum, Clostridium thermosaccharolyticum, Eubacterium limosum,* and *Peptostreptococcus productus*.

12. The method according to claim 1, wherein the bioalcohol is ethanol.

* * * * *

UNITED STATES PATENT AND TRADEMARK OFFICE
CERTIFICATE OF CORRECTION

PATENT NO.        : 8,889,386 B2  
APPLICATION NO.   : 13/869677  
DATED             : November 18, 2014  
INVENTOR(S)       : Kim et al.

Page 1 of 1

It is certified that error appears in the above-identified patent and that said Letters Patent is hereby corrected as shown below:

In the claims:

Column 9,  
Line 3, "tetramethylorthosilicate" should read --tetraethylorthosilicate--.

Column 10,  
Line 13, "*formicaeetricum*" should read --*formicacetricum*--.

Signed and Sealed this  
Eleventh Day of August, 2015

Michelle K. Lee  
*Director of the United States Patent and Trademark Office*